(12) United States Patent
Martz et al.

(10) Patent No.: US 6,666,866 B2
(45) Date of Patent: Dec. 23, 2003

(54) SPINAL INTERVERTEBRAL IMPLANT INSERTION TOOL

(75) Inventors: Erik Martz, Howell, NJ (US); Perry Germakis, Manalapan, NJ (US); John Boyle, Montclair, NJ (US); Daryl Sybert, New Albany, OH (US)

(73) Assignee: Osteotech, Inc., Eatontown, NJ (US)

( * ) Notice: Subject to any disclaimer, the term of this patent is extended or adjusted under 35 U.S.C. 154(b) by 197 days.

(21) Appl. No.: 10/086,041

(22) Filed: Oct. 25, 2001

(65) Prior Publication Data

US 2002/0188295 A1 Dec. 12, 2002

Related U.S. Application Data

(60) Provisional application No. 60/246,297, filed on Nov. 7, 2000.

(51) Int. Cl.[7] .............................................. A61B 17/70
(52) U.S. Cl. ...................................... 606/61; 623/17.16
(58) Field of Search .................. 606/61, 99; 623/17.11, 623/17.16

(56) References Cited

U.S. PATENT DOCUMENTS

| | | | |
|---|---|---|---|
| 4,736,738 A | 4/1988 | Lipovsek et al. | |
| 4,878,915 A | 11/1989 | Brantigan | |
| 4,904,261 A | 2/1990 | Dove et al. | |
| 5,192,327 A | 3/1993 | Brantigan | |
| 5,443,514 A | 8/1995 | Steffee | |
| 5,522,899 A | 6/1996 | Michelson | |
| 5,653,762 A | 8/1997 | Pisharodi | |
| 5,716,415 A | 2/1998 | Steffee | |
| 5,716,416 A | 2/1998 | Lin | |
| 5,720,751 A | 2/1998 | Jackson | |
| 5,741,253 A | 4/1998 | Michelson | |
| 5,782,830 A | 7/1998 | Farris | |
| 5,885,299 A | 3/1999 | Winslow et al. | |
| 5,885,300 A | 3/1999 | Tokuhashi et al. | |
| 5,893,890 A | 4/1999 | Picharodi | 623/17 |
| 5,910,141 A | 6/1999 | Morrison et al. | |
| 6,004,326 A | 12/1999 | Castro et al. | |
| 6,033,405 A | 3/2000 | Winslow et al. | |
| 6,033,438 A | 3/2000 | Bianchi et al. | |
| 6,042,582 A | 3/2000 | Ray | |
| 6,063,088 A | 5/2000 | Winslow | |
| 6,066,174 A | 5/2000 | Farris | 623/17 |
| 6,174,311 B1 | 1/2001 | Branch et al. | |

FOREIGN PATENT DOCUMENTS

| | | |
|---|---|---|
| WO | WO 97/30666 | 8/1997 |
| WO | WO99/09914 | 3/1999 |
| WO | WO00/24327 | 5/2000 |

OTHER PUBLICATIONS

Cauthen, (1988) *Lumbar Spine Surgery.*
Freebody, *Anterior Interbody Fusion for Spondylolisthesis (Via Transperitioneal Approach).*
Peer, (1955) *Transplantation of Tissues,* vol. 1, Baltimore: The Williams & Wilkins Company.

*Primary Examiner*—David O. Reip
(74) *Attorney, Agent, or Firm*—Carella, Byrne, Bain, Gilfillan, Cecchi et al.; Elliot M. Olstein; William Squire

(57) ABSTRACT

An insertion tool for a C-shaped bone spinal wedge shaped intervertebral implant comprises an outer shank with a hollow core in which is placed a shaft with a threaded stud which passes through a bore in the shank at an implant insertion end of the shank. A flat extension member defines a plane and extends from the shank overlying the stud, the stud for receiving a threaded bore of the spinal implant. The shaft has a knob distal the stud for rotatably attaching the stud to the implant. The extension member abuts the implant at mating flat surfaces which are spaced by a medial recess formed by a portion of the medullary canal of a long bone. A cap slides over the shank at an end opposite the extension member to capture the shaft in the shank core. A guide rod is attached to a collar on the shank normal to the plane of the extension member to assist the surgeon in orienting the implant to the disc space orientation during insertion of the implant. The extension member prevents rotation of the implant and in some implementations may absorb insertion stresses to minimize damage to the implant during insertion.

17 Claims, 3 Drawing Sheets

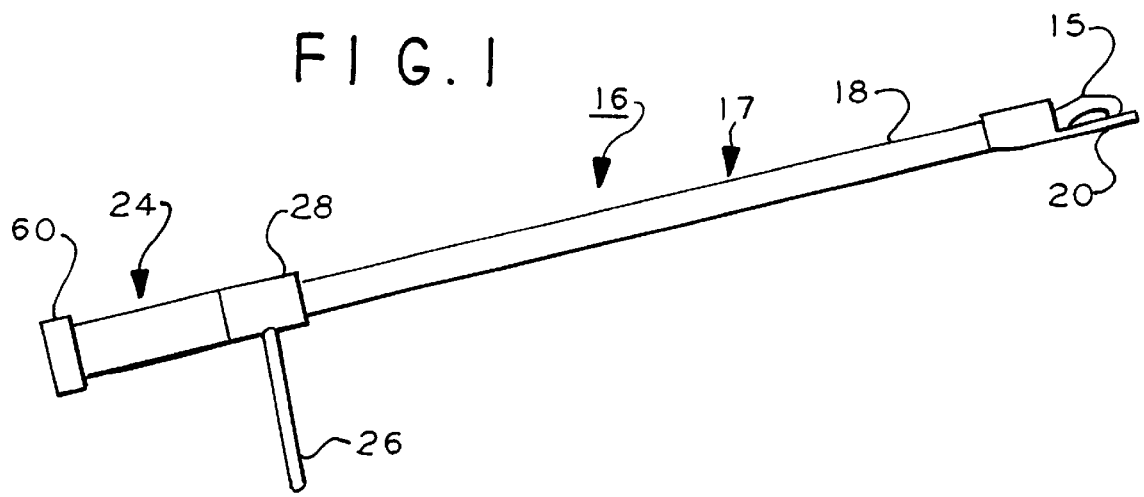
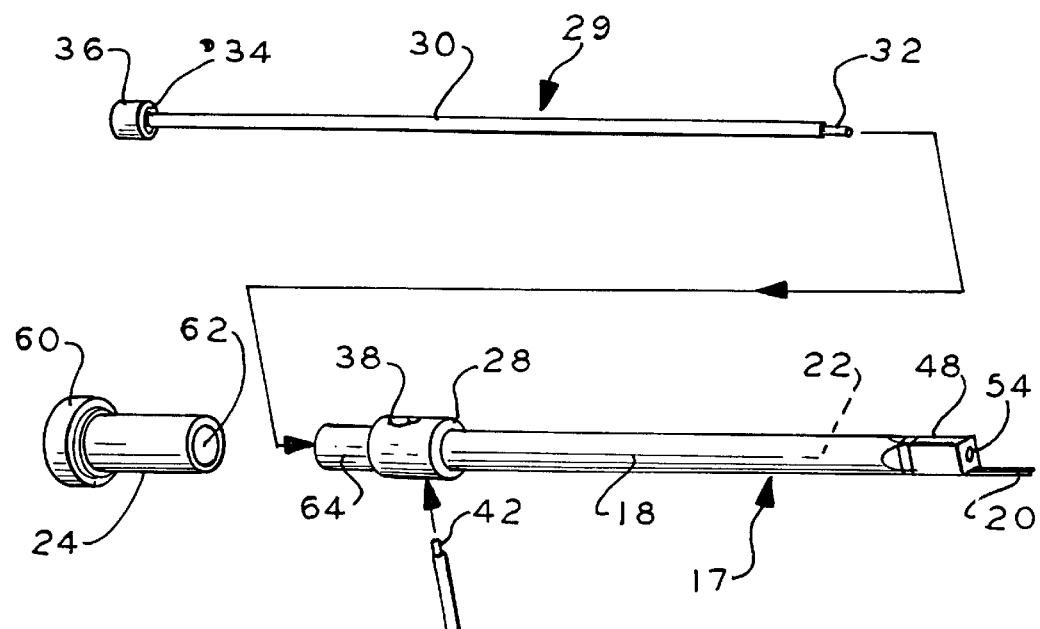
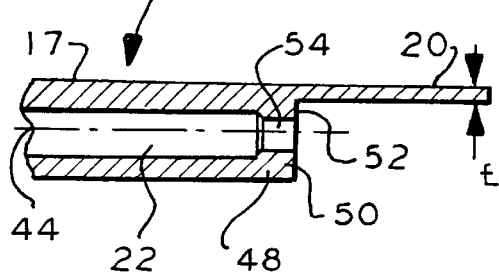
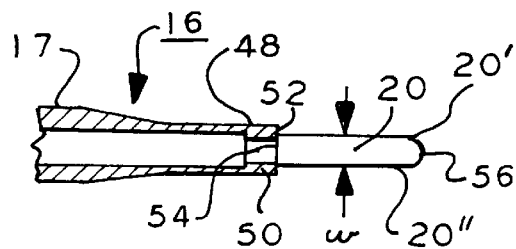

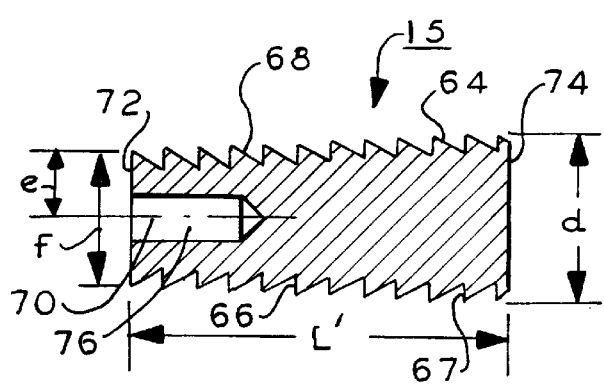
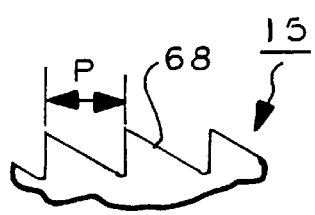
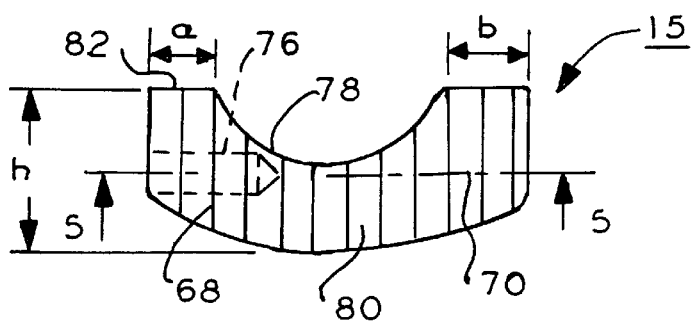
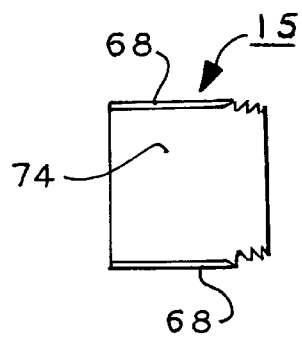
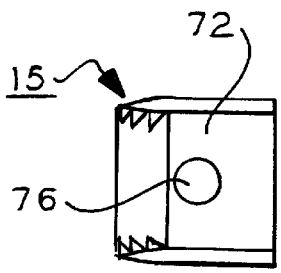
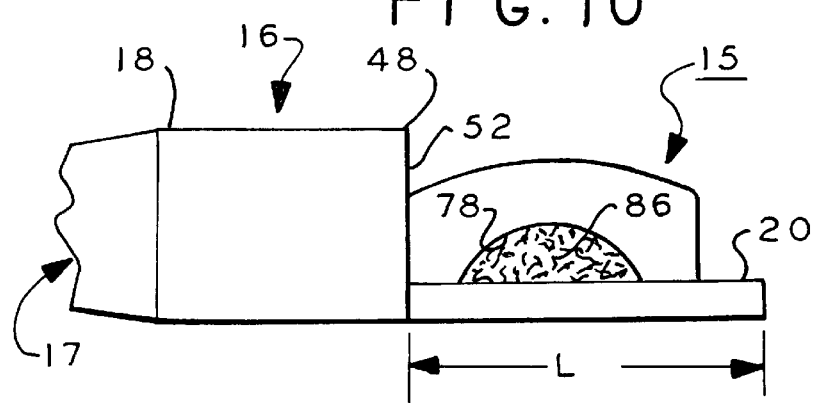

SPINAL INTERVERTEBRAL IMPLANT INSERTION TOOL

Priority is claimed on provisional application serial No. 60/246,297 filed Nov. 7, 2000.

This invention relates to spinal implant insertion tools for insertion of intervertebral fusion implants.

CROSS REFERENCE TO RELATED APPLICATION

Of interest is commonly owned copending application Ser. No. 09/328,242 entitled Ramp Shaped Intervertebral Implant filed Jun. 8, 1999 in the name of John W. Boyle incorporated by reference herein.

Surgical procedures for fusing adjacent vertebrae to treat various pathologies are well known. Implants for such procedures take a wide variety of shapes, forms and materials from bone to titanium inert materials, rigid and elastic, circular cylindrical, wedge shapes, cages with or without openings to accept bone fusion promoting material. The implant disclosed in the aforementioned application is preferred. The implants are dimensioned and shaped to provide a predetermined disc space between the fused adjacent vertebra.

Published PCT international applications WO 99/09914 and WO 00/24327 disclose C-shaped implants and tools related to surgery and to insertion of the implants.

U.S. Pat. No. 4,878,915 to Brantigan illustrates a spinal implant and insertion tool. The implant is circular cylindrical and has a threaded bore and two opposing radial slots at one end for receiving an insertion tool threaded stud and prongs. A sleeve with the prongs is slidably attached to the shaft of the insertion tool. The sleeve is advanced on the shaft of the stem of the tool to bottom the prongs on the sleeve in the slots in the implant.

U.S. Pat. No. 4,736,738 to Lipovsek et al. discloses an instrument kit and procedure for performing posterior lumbar interbody fusion.

U.S. Pat. No. 4,904,261 to Dove et al. illustrates an inert C-shaped spinal fusion implant.

U.S. Pat. No. 5,192,327 to Brantigan discloses a prosthetic implant for vertebrae. One or more plug implants are attached to an insertion tool by internally threaded hole in the plug. In the alternative, the plug may have a pair of side-by-side holes for receiving the tine end of a tool having a pair of tines. The tines engage the holes in the implant and thus require special holes for the insertion tool tines. In the alternative, the plug may have a threaded hole for receiving a threaded insertion tool.

U.S. Pat. No. 5,522,899 to Michelson discloses and insertion tool with a threaded portion for engaging a threaded opening in the implant. The engaging end of the insertion driver tool has a slightly convex surface to complement the surface of the implant and an extrusion for fitting within a depressed portion in the implant. The tool also has a restriction member for restricting the depth of penetration of the driver.

U.S. Pat. No. 5,653,762 ('762) discloses an applicator for an implant which is screwed into the implant. When the applicator is fully screwed in place, the implant is then inserted by the applicator.

U.S. Pat. No. 5,716,416 to Lin discloses insertion of an elastic intervertebral implant.

U.S. Pat. No. 5,720,751 discloses spinal insertion tools including a tool with opposing implant engaging portions and including a pusher assembly. In one embodiment the implant engaging portions are fixed and in other embodiments the insertion portion is formed of two arms secured in scissor-like fashion. A pusher may include a threaded stem for attachment to the handle for advancement of the pusher bar toward and away from the implant by rotation of the threaded stem.

U.S. Pat. No. 5,741,253 to Michelson, discloses a threaded self tapping spinal implant and insertion instrumentation. The implant is tubular and cylindrical and is inserted in an opening in the spine formed by a drill inserted in a sleeve.

U.S. Pat. No. 5,443,514 to Steffee discloses an instrument for holding and inserting a spinal implant and which includes an intermediate portion, a handle and a clamp portion. The implant is wedge shaped with two opposing flat parallel surfaces and two inclined surfaces which converge toward one end. The flat surfaces have recesses which receive the clamp of the instrument. The clamp comprises clamp halves with outwardly tapering surfaces and extensions which are received in the recesses. The extensions engage the flat bottom surfaces of the recesses. The clamp halves are drawn into mating inclined surfaces of the intermediate portion to force the clamp extensions against the implant recess bottom surfaces to compress the extensions against the implant. The insertion tool rotates the implant after it is inserted between adjacent vertebrae.

U.S. Pat. No. 5,782,830 to Farris discloses an implant insertion tool somewhat similar to the Steffee disclosure in that a pair of articulating jaws clamp an implant therebetween U.S. Pat. No. 6,033,438 discloses an open intervertebral spacer and tools and methods for insertion. The spacers have open mouth chambers. One spacer is an open-mouth plug from the diaphysis of a long bone forming a dowel disclosed as generally cylindrical. The chamber of the spacer has a truncated arm forming a channel for use with and for receiving an insertion tool. The channel permits osteogenic material to be packed within the chamber after implantation.

U.S. Pat. Nos. 5,885,299, 5,885,300, 5,910,141, 6,004,326, 6,033,405, 6,042,582 and 6,063,088 illustrate still other insertion tools for a spinal implant.

None of the above patents or applications address or recognize a problem with insertion of a C-shaped ramp as disclosed in the aforementioned copending application Ser. No. 09/328,242. In this ramp, a side of the implant is C-shaped and open. During surgery, it is desired to fill the C-shaped opening with fusion promoting material such as bone chips to facilitate bone fusion of the adjacent vertebrae in a posterior insertion procedure. Also during this procedure, two side by side spaced implants may be inserted into the evacuated disc space between two adjacent vertebra. One or two small openings may be made on the posterior side of the spinal region. Two implants are then inserted through the one opening on one side of the spinal cord or through a respective different one of two openings on opposing sides of the spinal cord. There is thus little room for the insertion tool The '438 patent attempts to address this problem.

Tools with articulated clamps need to have the clamps opened after the implant is inserted. Such opening requires the jaws to separate which may be detrimental to the surrounding tissue and also requires additional space in the disk space for such articulation. Some insertion tools attach to the implant solely by threads such as in the '762 patent. However, if the implant rotates during insertion, this may cause a problem.

As known, it is desired to fill the space around the implants with fusion promoting material such as bone chips and so on. However to fill the open space after the implants are inserted may be difficult. Even in those procedures where two openings are provided on each side of the spinal cord for separate implants, a problem of filling the space with bone growth promoting material to promote fusion may be difficult due to the small space available. In Pat. No. '438 an insertion tool is used with a truncated implant in which one arm is truncated relative to the other. The patent describes the fusion material as being added after insertion of the implant.

In respect to tools such as disclosed in the '438 patent, the present invention recognizes that the surgeon needs to align the implant with the disc space and such alignment with the disclosed tool may be difficult as the implant and tool interface are relatively small and may be difficult to align to the disc space.

The present invention is a recognition of these problems and is directed to provide a solution.

A spinal implant insertion tool according to the present invention is for inserting the implant into the disc space between two adjacent vertebra, the disc space having a given orientation relative to the spine, the implant having opposing first and second end surfaces and first and second opposing sides extending generally in a longitudinal direction between and toward the end surfaces, at least a third side having a flat surface located between the end surfaces, and a threaded bore in the first end surface. The tool comprises an elongated shank having a central longitudinal axis, the shank having an implant receiving surface at one end transverse to the axis for abutting the implant first end surface. An extension member extends from the one end in the axial direction and offset from the axis arranged to abut the third side surface of the implant. A threaded member extends axially from the implant receiving surface for engagement with the threaded bore, the extension member being arranged relative to the implant to preclude rotation of the implant relative to the shank about the axis. A guide member is secured to the shank and has a predetermined orientation relative to the extension member for providing visual alignment of the extension member relative to the disc space orientation during insertion of the implant.

In one aspect, the extension member has a flat surface for abutting the flat third side of the implant.

In a further aspect, the guide member comprises a rod extending from the shank at the predetermined orientation relative to the plane of the flat surface.

In a further aspect, the implant is C-shaped with a concave recess in the third side wall and forming fourth and fifth sides, the extension member having a length sufficient to overlap the concave recess of the received implant including the fourth and fifth sides and cooperating with the implant concave surface for entrapping bone growth material in the recess therebetween.

In a further aspect, a shaft is secured to the threaded member and rotatably secured to the shank for rotating the threaded member independently of the shank and extension member to secure the implant to the shank.

In a further aspect, a knob is secured to the shaft distal the threaded member for assisting in the manually gripping of the shaft and rotating the threaded member.

In a still further aspect, the shank comprises a tubular member with a hollow core, the shaft being rotatably mounted in the core.

Preferably, a bore is in the knob for receiving a rod transversely the shaft length to assist in the manual rotation of the knob.

In a further aspect, the extension member flat surface defines a plane, the shank including a transverse threaded bore spaced from the extension member for receiving and securing the guide member normal to the axis and normal to the plane.

Preferably the shank includes an annular collar extending about the shank periphery, the threaded bore being formed in the collar.

In a further aspect, the shank is tubular with a hollow core further including a shaft fixedly attached to the threaded member rotatably secured to the shank in the core, a collar surrounding the shank adjacent to the shank end distal the extension, the shank forming a sleeve between the shank end distal the extension and collar, and an end cap member secured to the sleeve for enclosing the core and shaft.

In a further aspect, the implant comprises a fourth side wall coextensive with the third side wall, the extension member for abutting the fourth side wall and for fully overlying said concave recess.

IN THE DRAWING

FIG. 1 is an isometric view of an implant insertion tool assembly with a representative implant attached according to an embodiment of the present invention;

FIG. 2 is an exploded view of the assembly of FIG. 1 without the implant attached;

FIG. 3 is a fragmented top sectional view of the insertion end of the tool of FIG. 2 as oriented during insertion of the implant with the plane of the tool normal to the disc space;

FIG. 4 is a fragmented side elevation sectional view of the insertion end of the tool of FIG. 2;

FIG. 5 is a side elevation sectional view of the implant of FIG. 7 taken along lines 5—5;

FIG. 6 is a more detailed side elevation fragmented view of a portion of the projections on a surface of the implant of FIG. 7;

FIG. 7 is a top plan view of the implant of FIG. 1;

FIG. 8 is an end elevation view of the implant of FIG. 7;

FIG. 9 is an end elevation view of the implant of FIG. 7 taken at the implant end opposite the end of the FIG. 8 view;

FIG. 10 is a more detailed top view of the insertion tool and implant of FIG. 1;

Figure 11:
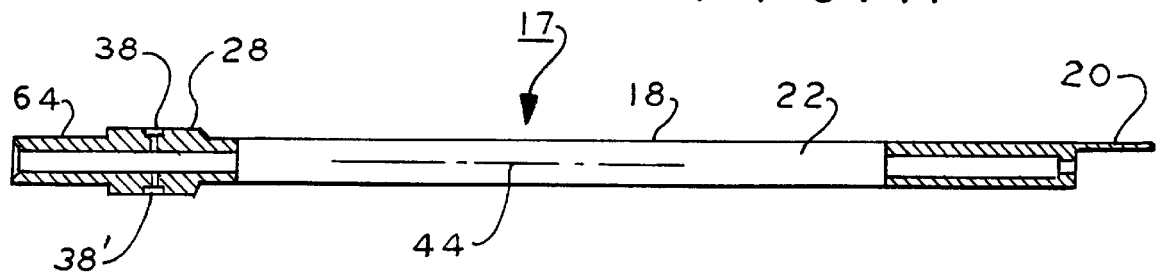
FIG. 11 is a top sectional view of the insertion tool shaft.
Figure 13:
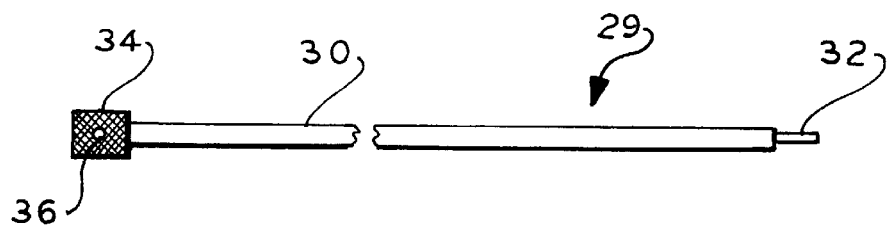
FIG. 13 is a fragmented side elevation view of the insertion tool threaded rod.

In FIGS. 1 and 2, implant 15 insertion tool 16 comprises an outer shank member 17 which includes an elongated tubular shank 18 having an extension tang-like member 20 at one end and a hollow core 22 (FIG. 11). A hollow cap 24 is attached to the shank 18 at its other end and encloses the core 22 at that end of the shank 18. An insertion guide rod 26 is attached to the shank 18 at annular collar 28 surrounding the shank 18. A shaft member 29 includes a shaft 30, FIGS. 2 and 13, has a threaded member stud 32 extending therefrom at one end of the shaft. The shaft member 29 is inserted into the core 22 of the shank 18. A knurled knob 34 is secured to the opposite end of the shaft 30 distal the stud 32. A through bore 36 is in the knob 34 and is adapted to receive a rod (not shown) therethrough transversely the longitudinal axis of the shaft 30. The rod (not shown) serves as a leverage and torque multiplier enhancement for rotating the shaft 30.

Figure 14:
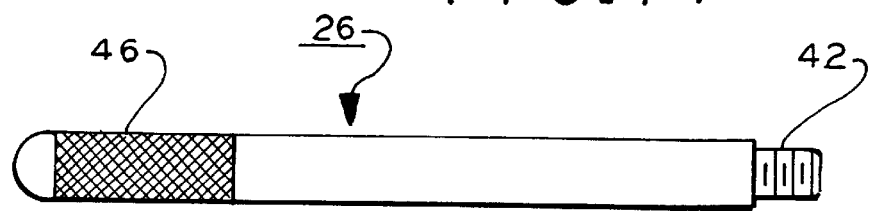
FIG. 14 is a more detailed side elevation view of a guide rod used with the insertion tool of FIG. 1.

In FIG. 11, the collar 28 is one piece integral with the shank 18 and is of larger diameter than the shank 18. The collar 28 has two aligned opposing like threaded bores 38, 38'. The insertion guide rod 26, FIG. 14, has a threaded stud 42 at one end which is engaged with one of the bores 38, 38', FIG. 2. The guide rod 26 is a circular cylindrical metal rod and extends normal to the longitudinal central axis 44 of the shank 18. The guide rod 26, FIG. 14, has knurls 46 to enhance gripping thereof. All of the components of the tool 16 are preferably stainless steel, but may be other materials.

The shank member 17, FIGS. 2, 3 and 4, includes a block member 48 secured to shank 18 at one end of the shank. The member 48 has a hollow core which is a continuation of and is in communication with the core 22 of the shank 18. The member 48 is square in transverse cross section relative to the axis 44 and has an end wall 50 preferably about 9 mm on a side. Wall 50 has a flat end surface 52 normal to axis 44. A through bore 54 on axis 44 passes through the end wall 50. The threaded member stud 32 of the shaft 30 passes through the wall 50 and is free to rotate in the bore 54 about axis 44. Extension member 20 extends from wall 50 offset from axis 44.

Extension member 20, FIGS. 3 and 4, has a thickness t and a width w. Width w, preferably about 4 mm, is greater than thickness t, preferably about 1.5 mm such that the extension member is paddle shaped. The extension member 20 is one piece and integral with the block 48. The width w may be more or less than the width of the block which in turn has sides of widths, e.g., 11 mm, that are smaller than the diameter of the shank 18. The block 48 may be about 0.4 inches (9–10 mm) on a side. The extension member has length L, FIG. 3, that is dimensioned relative to the implant length L', FIG. 5, to be described below. Generally, the length L is greater than (L'–b), FIG. 5, of all implants to be inserted by the tool 16. The length L needs to be sufficiently long to cover the recess 78, and preferably covering at least a portion of the surface 84. The extension member 20 has a rounded end surface 56, FIG. 4, in two orthogonal planes so that the end of the extension member is rounded in all planes.

Figure 12:
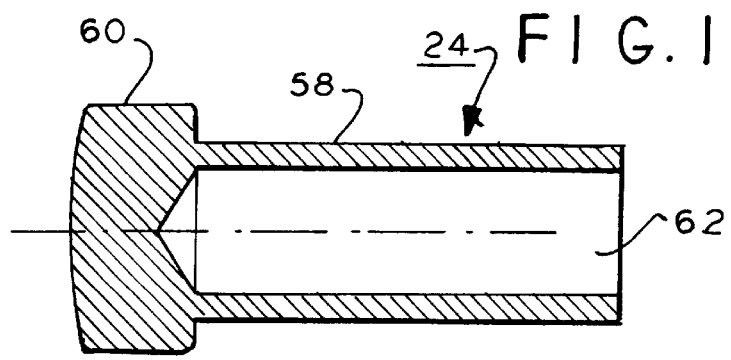
FIG. 12 is a side elevation view of the insertion tool cap for use with the shaft of FIG. 11.

End cap 24, FIG. 12, comprises an elongated sleeve 58 and a cap portion 60 of larger diameter than the sleeve 58. The sleeve 58 has a hollow core 62. The core 62 is dimensioned to slide over the outer surface of shank 18 end portion 64 as shown in FIG. 1. The knob 34 of the shaft member 29 fits within the core 62 of the cap 24 and extends beyond the shank. The knob 34 is pressed against and abuts the rear end surface of the shank 18 when the threaded stud is attached to the implant threads. This locks the shaft member 29 axially in place in the core 22 of the shank 18.

The implant 15, FIGS. 5 and 7, which may be referred to as a graft, is made of bone and is described in more detail in the aforementioned patent application Ser. No. 09/328, 242 incorporated by reference herein. The implant 15 has a top surface 64 and a bottom surface 68. These surfaces have serrations in the form of repetitive identical ridges or saw teeth 68. The saw teeth 68 have a pitch p, FIG. 6, which is determined for a given implant configuration. The surfaces 64 and 66 are inclined relative to the implant longitudinal axis 70 with a wider anterior end 74 and a narrower posterior end 72. End 74 is inserted first between the adjacent vertebra in the posterior approach. Surfaces 64 and 66 converge at posterior end 72 to height f in the range of about 7 to 13 mm from anterior height d in the range of about 9 to 15 mm at anterior end 74 in one embodiment. Dimension e is about 3.5 to about 6.5 mm in this embodiment.

The implant 15 has a threaded bore 76 in communication with posterior end 72. The bore 76 receives the threaded stud 32, FIG. 13, of the shaft member 29. Bore 76 is concentric with axis 70 and with the shank 18 axis 44 when the stud 32 is attached.

In FIG. 7, the implant 15 has a curved semi-circular recess 78 in the body 80 of the of the implant. The recess 78 may be formed in part from the intramedullary canal in a long bone, and the recess may be machined to the desired shape. The implant is formed from the diaphysis or metaphysis of a long bone. The cortical ring is secured within a holding fixture and the sidewalls of the cortical ring are machined to provide the implant with the desired shape. The intramedullary canal may form the recess 78 which extends for the height d in communication with surfaces 64 and 66 on one side of the implant. The implant is formed from human or animal bone such as the fibula, radius, ulna, humerus, tibia or femur. Reference is made to the aforementioned copending application Ser. No. 09/328,242 incorporated by reference herein in its entirety for more detail in regard to the implant 15 and its manufacture. The implant 15 longitudinal axis 70 extends along the length of its body 80.

The implant 15 has two spaced surfaces 82 and 84 separated by the recess 78. The surfaces 82 and 84 are flat and coplanar. Surface 82 has a face dimension a such that at least two full ridges of the teeth 68 span the dimension a. Dimension b also is of a minimum length so that at least two full ridges of the teeth 68 span this dimension as well. Dimension h is about 8.5 mm in this embodiment. The length dimension L' is about 20 to about 23 mm. These dimensions are given by way of example, as other dimensions may be used according to a given implementation and procedure being performed. The processing of the bone including demineralization, treatment with bone growth enhancing factors or other appropriate processes is discussed in more detail in the aforementioned copending application.

In operation, in FIG. 2, the shaft 29 is inserted into the core 22 of the shank 18. The threaded stud 32 is passed through the bore 54 of the block member 48 on the end of the shank 18. In FIG. 10, the implant 15 is then attached to the stud 32 at threaded bore 76 (FIG. 7) by rotation of the knob 34. An additional rod (not shown) attached to bore 36 in the knob 34 (FIG. 2) may be used to assist in tightening the stud to the implant 15 bore 76. The two spaced flat surfaces 82 and 84 of the implant abut a side surface of the extension member 20 and prevent the implant 20 from rotating while the stud 32 is tightened. The extension member 20 has a length L greater than the length (L'–b) of the implant 15. In this way, the extension member 20 completely overlies and encloses the recess 78 on a side opposite the body 80 in a plane parallel to the plane of the drawing in FIG. 10. The recess 78 later prior to implantation is filled with bone growth promoting material 86 which is retained by the body 80 and extension member 20 in that plane.

Once the stud 32 is attached to the implant 15, the cap 24 is then slid over the end of the cylindrical surface 64 of the shank 18, FIG. 2, captivating the shaft 30 in the shank 18 core 22. Guide rod 26 is attached to the shank collar 28 to assist the surgeon in insertion of the implant 15 during the surgery. The guide rod 26 has a longitudinal axis that is normal to the longitudinal axis of the shank 18. Most importantly, the plane of the flat surfaces of the extension member 20, FIG. 11, is also normal to the longitudinal axis of the guide rod 26 as determined by the orientation of the threaded bores 38, 38' which receive the threaded stud of the guide rod 26. The plane of the extension member 20 during insertion of the implant is generally oriented parallel to the spine length. That is, the edges 20' and 20" of the extension member 20 each engage a different one of the two adjacent vertebra to be fused if the width w of the extension member 20, FIG. 4, is greater than that of the height d, FIG. 5, of the implant. With the extension member 20 so oriented relative to the spine the guide rod 26 is at right angles to this orientation. The guide rod in this orientation thus lies in a plane generally parallel to the disc plane. Assuming the plane of the extension member passes through the six and twelve o'clock positions parallel to the spine length direction, the plane of the guide member 26 passes through the three and nine o'clock positions. Because the end of the insertion extension member is small as is the implant, the orientation of the guide rod significantly helps the surgeon orient the implant as desired.

The extension member 20 also serves an important function of supporting the implant 15 during insertion into the intervertebral space. When the length of the extension member 20 overlaps the recess 78 and surfaces 82 and 84 of the implant, then the extension member absorbs bending inducing forces and helps protect the implant at this critical time of the process. The implant-extension member relationship when the extension member is larger than the corresponding implant relative dimensions provides implant support during the insertion into the disc space prepared in a known manner.

In another embodiment, when the extension member 20 width w is greater than height dimension d of the implant, FIG. 5 (in and out of the drawing figure, FIG. 10), the extension member 20 by initial contact with the vertebra at the top edge 20' and bottom edge 20", FIG. 4, receives the initial insertion forces, and thus tends to minimize implant stress during insertion along with the length relation previously described. This action occurs when the vertebra are distracted a distance less than the extension member width w between the member 20 top and bottom edges and the extension member width w, FIG. 4, is greater than the dimension d, FIG. 5, of the implant 15.

The end cap 24 may be used for insertion by sliding the cap on the shank 18 end and impacting the cap 24 on the collar 28 in the insertion direction. The surgeon aligns the implant and extension member to the disc space using the guide rod 26. The cap is impacted against the collar 28 gently inserting the implant into the evacuated disc space. The disc space may also include channels in the adjacent vertebra end plates formed by chisels (not shown), the channels for receiving the implant.

After the implant is inserted, the cap 24 is removed, and the threaded stud 32 of the shaft 29 is disengaged from the implant. Then the extension member is removed from the disc space. Should it be desired to place a second implant adjacent to the just inserted implant, the process is repeated. The bone promoting material such as bone chips and the like in the implant recess 78 remain with the implant after the extension member is removed. Bone promoting material may then be added by the surgeon to further fill in the disc space surrounding the inserted implant or implants.

In the case of implants without the recess 78, then the extension member 20 may abut a surface of the implant partially as well as over its entirety. It is preferable to support the implant over its full length to minimize stress damage to the implant during insertion and protect the implant. The use of a single extension member occupies a minimum of space which is typically small without excessive room for insertion tools. The extension member also assists in preventing rotation of the implant relative to the insertion tool 16 which may occur without the extension member. The implant surface 72, FIGS. 7 and 9, is flat so as to engage the flat end surface 52 of the block 48, FIGS. 3 and 4. This helps maintain the implant stable and immobile during insertion.

It will occur to one of ordinary skill that modifications may be made to the disclosed embodiments without departing from the scope of the invention as defined in the appended claims. The disclosed embodiments are given by way of illustration and not limitation.

For example, the extension member preferably is longer than the implant so as to engage both surfaces of the implant on each side of the recess 78. However, the extension member may also abut only one surface such as surface 82, FIG. 7, and still overlie substantially the entire extent of the recess 78 between the surfaces 82 and 84. By abutting the extension member 20 with both surfaces 82 and 84 of the implant, greater support and resistance to stress is provided the implant. The threaded stud 32 holds the implant in place regardless of the relative configuration of the extension member to the implant as long as at least one of the two implant surfaces 82 and 84 abut the extension member.

What is claimed is:

1. A spinal implant insertion tool for inserting the implant into the disc space between two adjacent vertebra, the disc space having a given orientation relative to the spine, the implant having opposing first and second end surfaces and first and second opposing sides extending generally in a longitudinal direction between and toward the end surfaces, at least a third side having a flat surface located between the end surfaces, and a threaded bore in the first end surface, the tool comprising:

an elongated shank having a central longitudinal axis, the shank having an implant receiving surface at one end transverse to the axis for abutting the implant first end surface;

an extension member extending from the one end in the axial direction and offset from the axis arranged to abut the third side surface of the implant, the extension member being arranged relative to the implant to preclude rotation of the implant relative to the shank about the axis;

a threaded member extending axially from the implant receiving surface for engagement with the threaded bore; and a guide member secured to the shank having a predetermined orientation relative to the extension member for providing visual alignment of the extension member relative to the disc space orientation during insertion of the implant.

2. The tool of claim 1 wherein the extension member has a flat surface for abutting the flat third side of the implant.

3. The tool of claim 2 wherein the guide member comprises a rod extending from the shank at the predetermined orientation relative to the plane of said flat surface.

4. The tool of claim 3 wherein the extension member flat surface defines a plane, the shank including a transverse threaded bore spaced from the extension member for receiving and securing the guide member normal to the axis and normal to the plane.

5. The tool of claim 4 wherein the shank includes an annular collar extending about the shank periphery, the threaded bore being formed in the collar.

6. The tool of claim 1 wherein the implant is C-shaped with a concave recess in the third side wall and forming fourth and fifth sides, the extension member having a length sufficient to overlap the concave recess of the received implant including at least a portion of the fourth and fifth sides and cooperating with the implant concave surface for entrapping bone growth material in the recess therebetween.

7. The tool of claim 6 wherein the implant comprises a fourth side wall coextensive with the third side wall, the extension member for abutting said fourth side wall and for fully overlying said concave recess.

8. The tool of claim 1 including a shaft secured to the threaded member and rotatably secured to the shank for rotating the threaded member independently of the shank and extension member to secure the implant to the shank.

9. The tool of claim 8 including a knob secured to the shaft distal the threaded member for assisting in the manually gripping of the shaft and rotating the threaded member.

10. The tool of claim 9 further including a bore in said knob for receiving a rod transversely the shaft length to assist in the manual rotation of the knob.

11. The tool of claim 8 wherein the shank comprises a tubular member with a hollow core, said shaft being rotatably mounted in said core.

12. The tool of claim 1 wherein the shank is tubular with a hollow core further including a shaft fixedly attached to the threaded member rotatably secured to the shank in the core, a collar surrounding the shank adjacent to the shank end distal the extension, the shank forming a sleeve between the shank end distal the extension and collar, and an end cap member secured to the sleeve for enclosing the core and shaft.

13. A spinal implant insertion tool comprising:
   a tubular shank having a longitudinal axis and a hollow core terminating at one end in an end surface with a bore therethrough along said axis;
   a collar extending about the shank adjacent to one shank end;
   a guide member extending normal to the shank and attached to the collar;
   a shaft rotatably mounted in the core with a threaded member at one end and extending through the bore;
   a flat elongated extension member defining a plane fixedly secured to and extending from the shank one end offset from the axis, the plane being at a predetermined orientation relative to the guide member; and
   a cap attached to the shank at an end distal said extension member for releaseably enclosing said core and received shaft.

14. The tool of claim 13 wherein the guide member has a longitudinal axis that is normal to the plane of the extension member.

15. A spinal implant insertion tool for inserting the implant into the disc space between two adjacent vertebra, the disc space having a given orientation relative to the spine, the implant having opposing first and second end surfaces and first and second opposing sides extending generally in a longitudinal direction between and toward the end surfaces, third and fourth coplanar flat sides spaced by an intervening chamber in communication with the first, second, third and fourth sides and located between the third and fourth sides, the third side located adjacent to the first end and the fourth side located adjacent to the second end, and a threaded bore in the first end surface, the tool comprising:
   an elongated shank having a central longitudinal axis, the shank having an implant receiving surface at one end transverse to the axis for abutting the implant first end surface;
   an extension member extending from the one end in the axial direction and offset from the axis arranged to abut the third and fourth sides surfaces and over lie the chamber; and
   a threaded member extending axially from the implant receiving surface for engagement with the threaded bore, the extension member being arranged relative to the implant to preclude rotation of the implant relative to the shank about the axis.

16. The tool of claim 15 further including a guide member secured to the shank having a predetermined orientation relative to the extension member for providing visual alignment of the extension member relative to the disc space orientation during insertion of the implant.

17. The tool of claim 15 wherein the threaded member comprises a rod secured thereto including a knob for rotation of the threaded member independently of the shank.

* * * * *